(12) United States Patent
Knapp et al.

(10) Patent No.: US 6,964,669 B1
(45) Date of Patent: Nov. 15, 2005

(54) LINEAR DELIVERY SYSTEM FOR DEPLOYMENT OF A DETACHABLE BALLOON AT A TARGET SITE IN VIVO

(75) Inventors: Tracey Knapp, Tucker, GA (US); John Frigstad, Coralville, IA (US); Paul Volpini, Cedar Rapids, IA (US); Charles Goudy, North Liberty, IA (US)

(73) Assignee: AMS Research Corporation, Minnetonka, MN (US)

( * ) Notice: Subject to any disclaimer, the term of this patent is extended or adjusted under 35 U.S.C. 154(b) by 0 days.

(21) Appl. No.: 09/547,952

(22) Filed: Apr. 12, 2000

(51) Int. Cl.[7] .............................................. A61M 29/00
(52) U.S. Cl. ..................................................... 606/192
(58) Field of Search .............................. 606/108, 170, 606/171, 174, 180, 191–198

(56) References Cited

U.S. PATENT DOCUMENTS

| | | | |
|---|---|---|---|
| 2,513,014 A | 6/1950 | Fields | |
| 2,856,920 A | 10/1958 | Indelicato | |
| 3,795,246 A | 3/1974 | Sturgeon | 128/325 |
| 3,831,585 A | 8/1974 | Brondy et al. | 128/2 B |
| 3,834,394 A | 9/1974 | Hunter et al. | 128/325 |
| 4,019,499 A | 4/1977 | Fitzgerald | 128/1 R |
| 4,240,433 A | 12/1980 | Bordow | 128/347 |
| 4,282,875 A | 8/1981 | Serbinenko et al. | 128/325 |
| 4,327,734 A | 5/1982 | White, Jr. | 128/325 |
| 4,334,327 A | 6/1982 | Lyman et al. | 3/1 |
| 4,341,218 A | 7/1982 | U | 128/325 |
| 4,346,712 A | 8/1982 | Handa et al. | 128/325 |
| 4,364,392 A | 12/1982 | Strothers et al. | 128/325 |
| 4,402,319 A | 9/1983 | Handa et al. | 128/325 |
| 4,429,724 A | 2/1984 | Dorros et al. | 141/27 |
| 4,441,495 A | 4/1984 | Hicswa | 128/325 |
| 4,517,979 A | 5/1985 | Pecenka | 128/325 |
| 4,520,823 A | 6/1985 | LeVeen et al. | 128/348.1 |
| 4,545,367 A | 10/1985 | Tucci | 128/1 R |
| 4,557,255 A | 12/1985 | Goodman | 128/7 |
| 4,559,043 A | 12/1985 | Whitehouse et al. | 604/201 |
| 4,773,393 A | 9/1988 | Haber et al. | 600/30 |
| 5,007,898 A | 4/1991 | Rosenbluth et al. | 604/54 |
| 5,071,429 A | 12/1991 | Pinchuk et al. | 606/192 |
| 5,078,681 A | 1/1992 | Kawashima | 604/53 |
| 5,222,970 A | 6/1993 | Reeves | 606/195 |
| 5,306,284 A * | 4/1994 | Agee et al. | 606/170 |
| 5,458,615 A * | 10/1995 | Klemm et al. | 606/198 |
| 5,637,074 A | 6/1997 | Andino et al. | |
| 6,786,918 B1 * | 9/2004 | Krivoruchko et al. | 606/198 |

FOREIGN PATENT DOCUMENTS

| | | |
|---|---|---|
| FR | 2.050.875 A | 4/1971 |
| WO | WO 8800070 | 1/1988 |
| WO | WO 8900030 | 1/1989 |
| WO | WO 9307815 | 4/1993 |

* cited by examiner

*Primary Examiner*—Kevin T. Truong
(74) *Attorney, Agent, or Firm*—Barbara A. Wrigley; Oppenheimer Wolff & Donnelly; José W. Jimenez (57) ABSTRACT

A linear delivery system and method for deployment of a detachable balloon at a target site in a patient in vivo is disclosed. The system includes a unitary sheath assembly having a retractable shaft and base, and a balloon delivery device configured for insertion through the lumen of the sheath assembly. The linear method of delivery overcomes disadvantages and limitations caused by undesirable movement of the assembly or separation of the catheter from the delivery system during inflation of the balloon. The linear delivery system further includes properties that increase the ease of use and stability of the device so as to reduce the effort required by the physician and discomfort experienced by the patient during deployment of a detachable balloon.

11 Claims, 10 Drawing Sheets

LINEAR DELIVERY SYSTEM FOR DEPLOYMENT OF A DETACHABLE BALLOON AT A TARGET SITE IN VIVO

FIELD OF THE INVENTION

The present invention relates generally to a system for deployment of a detachable balloon in medical procedures. The present invention particularly relates to a linear delivery system for deployment of detachable, inflatable balloons in medical procedures involving blood vessels, body cavities, treatment of urinary incontinence, and the like.

BACKGROUND OF THE INVENTION

Detachable balloons are used for a wide variety of medical procedures where occlusion of a vessel or duct, or compression at a target tissue site is desired. One specific example is in the treatment of urinary incontinence. In patients suffering from this condition, detachable balloons have been used to successfully treat the bladder sphincter deficiency. One or more detachable balloons are implanted into the tissue adjacent to the neck of the bladder of a patient. The inflated balloons aid in the ability of the bladder sphincter muscles to occlude, which improves or resolves the condition. This method of treatment is preferred as it is minimally-invasive, safe and less traumatic to the patient. As such, various systems have been developed for the delivery of balloon catheters to a desired target site. See, for example, U.S. Pat. No. 5,411,475; U.S. Pat. No. 4,802,479; and U.S. Pat. No. 4,686,962.

Haber et al., U.S. Pat. No. 4,832,680 describe an apparatus and a non-surgical method for treatment of urinary incontinence. The method entails use of a hypodermic needle to implant a balloon in the tissue adjacent to the urethra. Specialized instrumentation is required to aid in positioning the balloon and protecting the balloon during insertion into the patient's tissue. A particular disadvantage in this system is that it is cumbersome and difficult to maneuver and requires complicated instrumentation for protection of the balloon during delivery. As a result, more simple and effective balloon delivery systems have been developed.

An example of such a device may be found in U.S. Pat. No. 5,830,228, which describe a system for delivering a detachable, inflatable balloon at a target site. The system includes a holder, a protective sheath configured for insertion through the holder and a hub at the proximal end of the sheath; a delivery device for carrying a balloon; and a retractor located on the delivery device for withdrawing the sheath. The retractor includes a head which withdraws the hub of the sheath by movement of the head. Use of the system requires insertion of the protective sheath through the holder and retraction of the sheath by rotating the head of the retractor which is located on the delivery device. Internal threads within the head aid in withdrawing the sheath by engaging in external threads on the hub of the sheath.

The above-described delivery systems (and other similar devices not specifically described) offer advantages, including effectiveness and safety to both the user and the patient. However, it has been discovered that an obstacle or disadvantage to such devices is the requirement for specialized instrumentation or that their use is complicated. Additionally, even with the more simple delivery system, the susceptibility of separation of certain component parts, such as the catheter and/or the positioning element, from the delivery system during use in the patient result in major limitations to the reliability of the system. Further, the motion required for retraction of the sheath to expose the balloon is a difficult and more cumbersome motion to perform. Yet still further, the rotational movement necessary to remove the needle (or positioning element) is likely to cause undesirable tissue trauma.

In view of the above, it is apparent that there is a need to provide a delivery system with a more reliable and stable delivery of inflatable, detachable balloons. There is also a need to provide a delivery system that is efficient, simpler to use for the physician and easy to implement. A reliable and efficient delivery system would reduce the overall procedure time required and therefore reduce patient discomfort. Such delivery systems include properties that reduce the amount of effort required by the physician prior to and during use of the system as well as properties that ensure the system remain intact during insertion into the target tissue and during inflation of the balloon.

OBJECTS AND SUMMARY OF THE INVENTION

In view of the foregoing, it is an object of the present invention to provide a balloon delivery device that addresses the limitations and disadvantages associated with prior delivery devices, yet meets the needs of the users.

A further object of the invention is to provide a linear delivery system that is efficient, requires minimal effort by the user, is easy to assemble and disassemble, and that is reliable.

Still another object of the invention is to provide a linear delivery system that minimally obstructs the surgeon's view of the target site.

A further object of the invention is to provide a linear delivery system having flexible guide tabs which prevent separation of the catheter or positioning element from the delivery system during use.

A further object of the invention is to provide a linear delivery system configured so that retraction of the shaft is maintained along a longitudinal axis and is accomplished by a single motion.

A further object of the invention is to provide a linear delivery system that has a single-unit sheath assembly.

In one aspect of the invention, a linear delivery system for deploying a detachable, inflatable balloon to a target site in a patient is disclosed. The system can include a unitary sheath assembly having a retractable shaft portion and a base portion. The retractable shaft portion can have an inner lumen that is between a proximal and a distal end of the retractable shaft. The base portion of the unitary sheath assembly has a lumen that is between a first and second end of the base portion. The proximal end of the shaft portion can be moveably coupled to the second end of the base portion. A retraction tab that is moveable can be located between the first and second ends of the base portion and coupled to the shaft portion of the unitary sheath assembly. The shaft portion of the unitary sheath can be withdrawn toward the first end of the base portion upon movement of the switch. A linear delivery system can also have a balloon delivery device configured for insertion through the lumen of the sheath assembly; the delivery device having a catheter, a hub and a guide tab coupled to the hub.

An additional object of the invention is to provide a method of deploying a detachable, inflatable balloon at a target site in a patient in vivo using a linear delivery system.

These and other objects not specifically enumerated herein are believed to be addressed by the present invention which contemplates a linear delivery system for deploying a detachable, inflatable balloon that includes a unitary sheath assembly having a retractable shaft and base portion and a balloon delivery device.

DETAILED DESCRIPTION OF THE INVENTION

Figure 1:
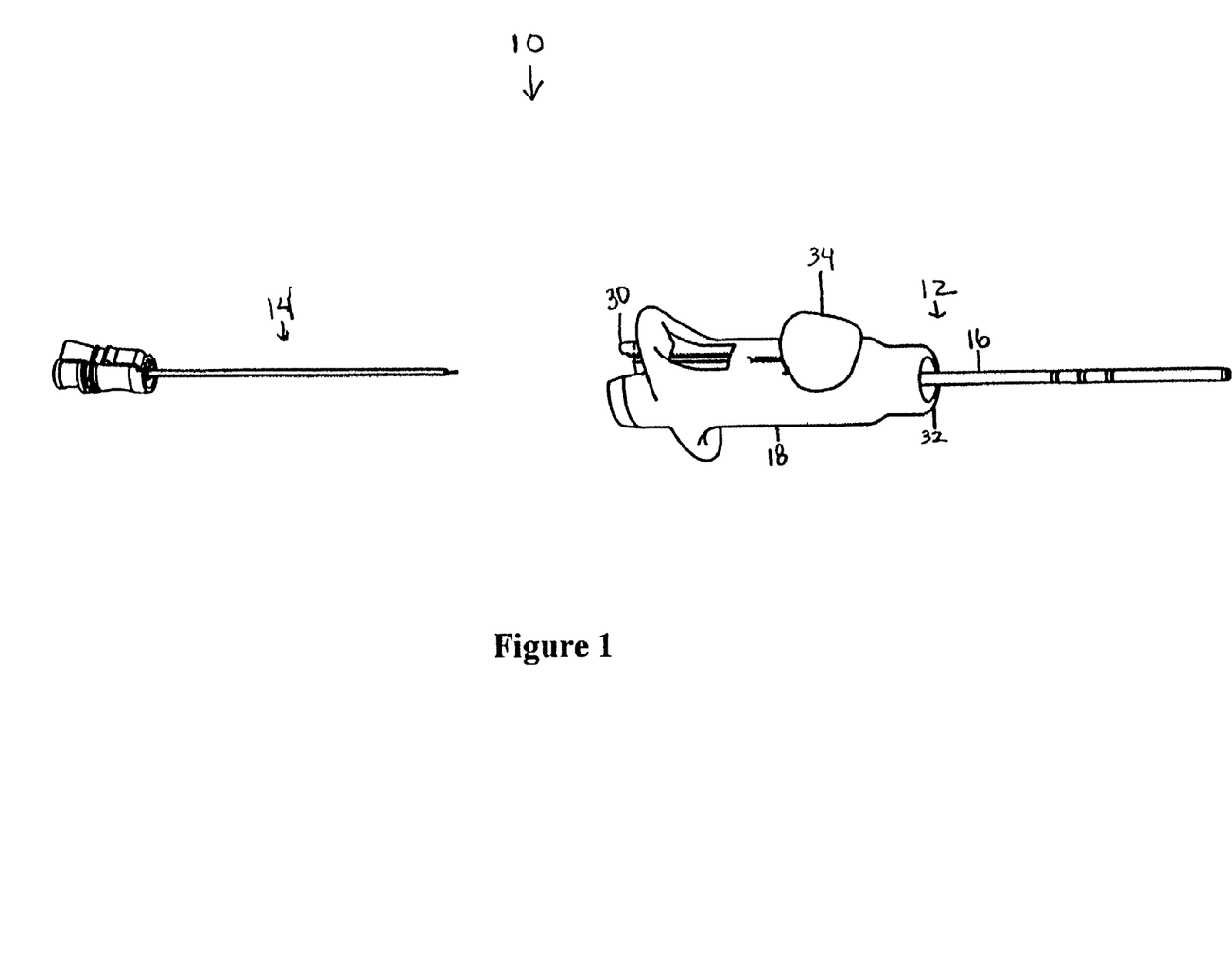
FIG. 1 is an exploded side view of a preferred embodiment of the present invention including a unitary sheath assembly having a retractable shaft portion and a base portion, and a balloon delivery device.

FIG. 1 shows an exploded side view a linear delivery device 10 for deploying a detachable inflatable balloon to a target site in vivo. The device includes a unitary sheath assembly 12 and a balloon delivery device 14. The unitary sheath assembly 12 has a retractable shaft portion 16 and a base portion 18. The unitary sheath assembly 12 should be a single unit device in that the retractable shaft portion 16 cannot be removed or separated from the base portion 18.

Figure 2:
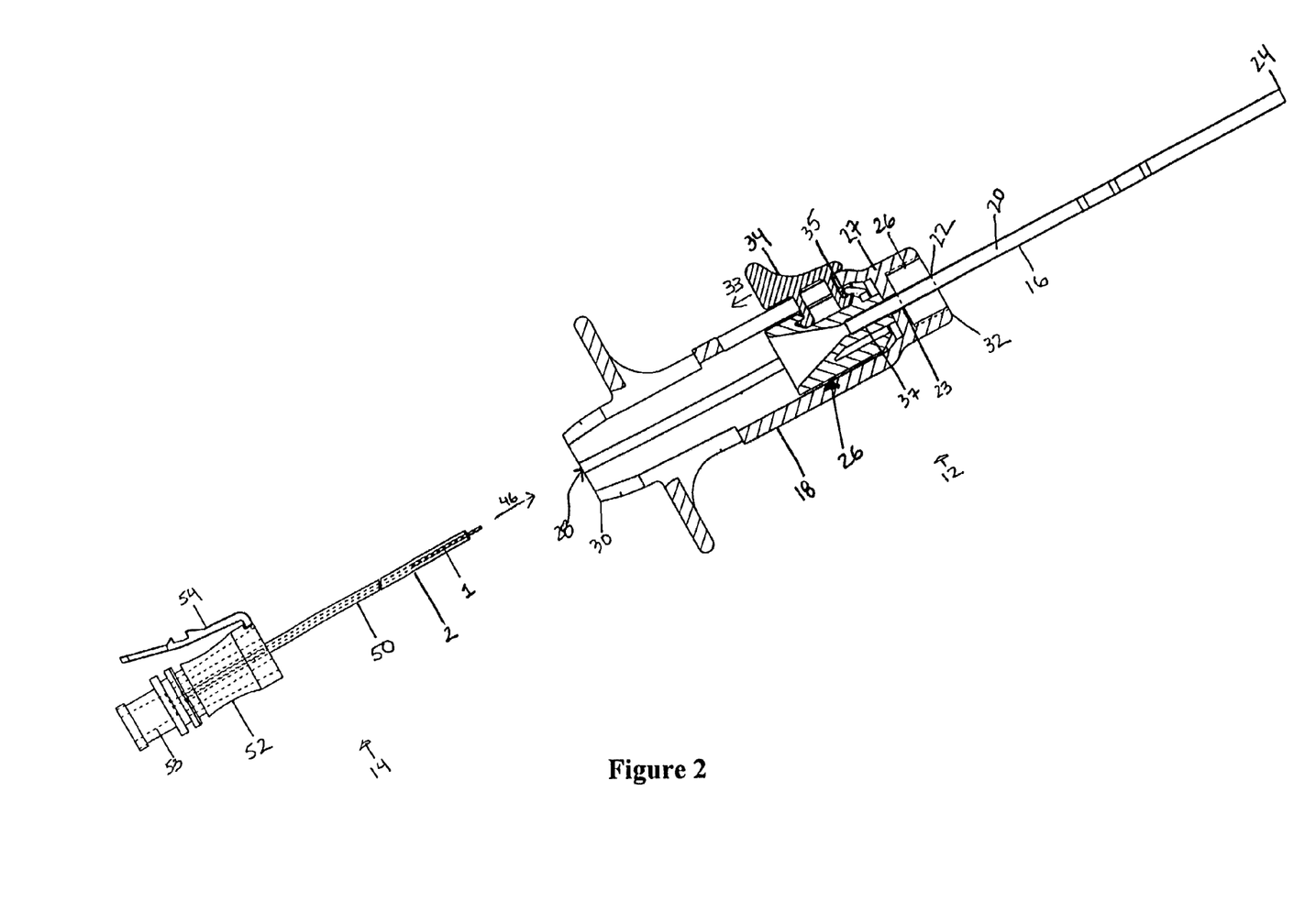
FIG. 2 is an additional side view of a unitary sheath assembly having a retractable shaft portion and a base portion, and a balloon delivery device.

Referring to FIG. 2, a more detailed view of a linear delivery device is shown. The retractable shaft portion 16 has an inner lumen 20 between a proximal end 22 and a distal end 24. The base portion 18 also has an inner lumen 28 between a first end 30 and a second end 32. As shown in FIG. 2, a retractable shaft portion 16 can also include a shaft hub 26 coupled to the proximal end 22 of the retractable shaft portion 16 and the second end 32 of the base portion 18. The shaft hub 26 resides within 27 the base portion at the second end 32 of the base portion 18 and is therefore, not visible to a viewer externally.

Figures 3, 3A:
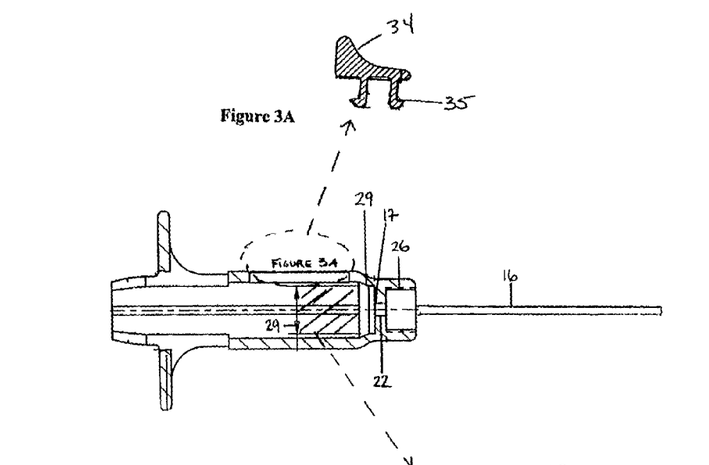
FIG. 3 is an exploded side view of unitary sheath assembly having a retractable shaft portion including a retracting tab component, a base portion including a connecting element and a shaft hub, and a shaft portion.

As shown in FIG. 1, a retracting tab or switch 34 is disposed between the first 30 and second 32 ends of the base portion 18. Referring now to FIG. 2, a retracting tab 34 is coupled to a connecting element 29 located toward the second end 32, within the base portion 18. The retracting tab 34 will also include a lower stem region 35 which is configured so as to allow its engagement to the connecting element 29 within the base portion 18. FIG. 3 shows additional views detailing the coupling of the connecting element 29 to the retracting tab 34 and proximal end 22 of the shaft portion 16.

Figure 3B:
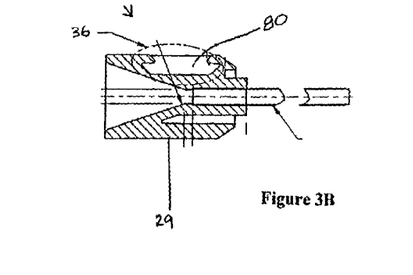

As shown in FIG. 3 and detailed in FIG. 3B, the connecting element 29 is also coupled 17 to the shaft portion 16 at the proximal end 22 of the shaft portion 16. This coupling occurs internally within the base portion 18. During use of the system, the shaft portion 16 of the linear delivery system 10 is retracted backward 33 by retraction of the retracting tab 34 (see FIG. 2). FIG. 3A shows an exploded side view of the retracting tab. The connecting element 29 is configured 36 to have a receptacle 80 so as to fit the configuration of the lower stem region 35 of the retracting tab 34. The coupling of the retracting tab 34 to the shaft portion 16 by a connecting element 29 allows for this feature. Coupling of the shaft hub 26 and the shaft portion 16 to the retracting tab 34 via the connecting element 29, also prevents separation of the shaft portion 16 from the base portion 18, which is further detailed below.

Figures 4, 4A:
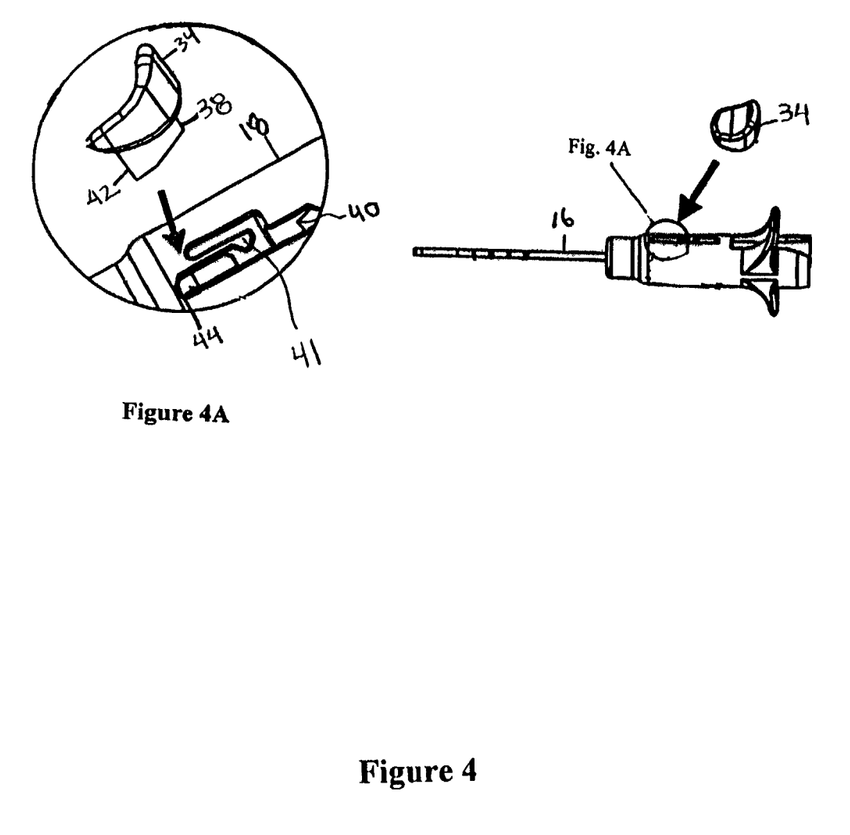
FIG. 4 is a detailed view of a retracting tab component of a unitary sheath assembly and a base portion having a slot opening.

FIG. 4 shows a side view of an embodiment of the linear delivery device. An enlarged view of a retracting tab 34 component of a unitary sheath assembly is shown in FIG. 4A. The stem 38 of the retracting tab 34 couples the retracting tab 34 to the hub (not shown) of the shaft portion 16 through a slot opening 40 on the base portion 18 of the unitary sheath assembly 12. The shaft portion is retracted or withdrawn into the lumen of the base portion by sliding the retracting tab 34 back toward the first end 30 (see FIG. 1) of the base portion 18. The mechanism of the retraction tab exposes the balloon to the target tissue by a linear delivery method. Use of linear delivery simplifies the motion required for retraction of the shaft and is an ambidextrous motion that can be performed by a physician using one hand.

Another aspect of the retracting tab that is advantageous to achieving the goals of the invention is the coupling of the retracting tab 34 to the connecting element 29 by a stem 38 of the retracting tab 34 through the slot opening 40 of the base portion. This coupling prevents separation of the shaft portion from the base portion due to the proximal end 42 of the stem abutting against the proximal end 44 of the slot opening and thus retaining the retraction tab 34 within the slot opening 40. The stem 38 of the retracting tab 34 can, if desired, be adhesively bonded to a receptacle 80 (FIG. 12A) of the connecting element 29, thereby further securing the shaft portion to the base 18 and retracting tab 34. Additionally, as shown in FIG. 4A, the slot opening 40 is configured with a bendable tong 41 to capture the retraction tab in either a full forward or a full backward position. This stabilizes retraction of the shaft during the step of exposing the balloon to a target site.

Figure 5:
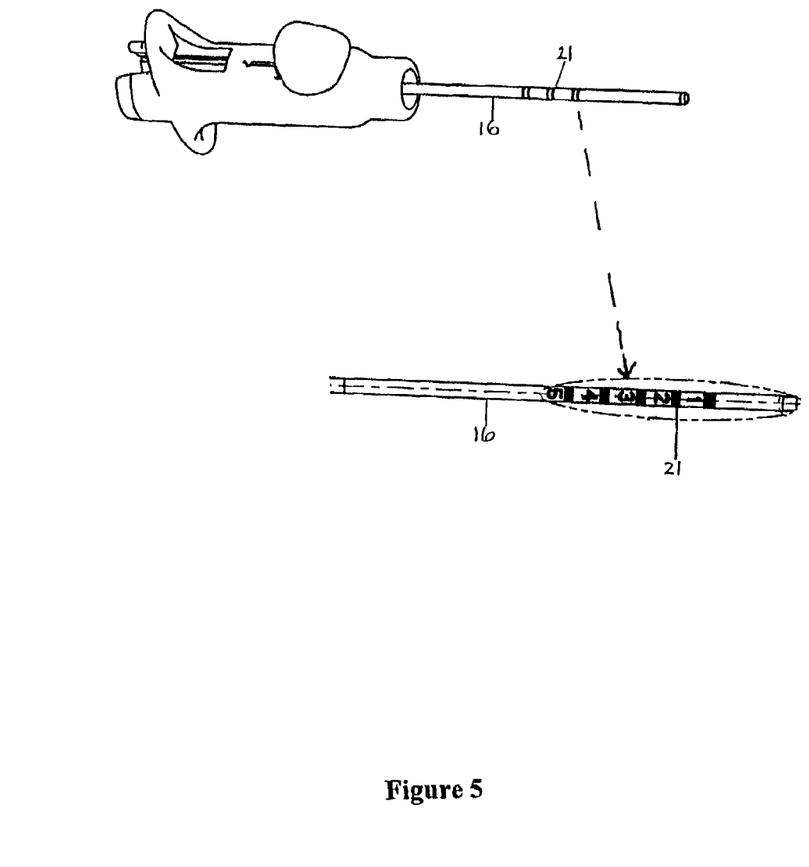
FIG. 5 is a top perspective view of a unitary sheath assembly with a more detailed view of a shaft portion having visual indicators.

In a preferred embodiment, visual indicators can be disposed on the sheath assembly for providing an indication of a penetration depth of the unitary sheath assembly into a patient. FIG. 5 shows a view of an embodiment of the invention, detailing a shaft portion 16 of the invention having visual indicators 21. In addition, a holding means or element 19 (see FIG. 6) can be disposed on the base portion 18 of the sheath assembly for attachment of the assembly to a viewing instrument. Such a holding element can be achieved, for example, by a use of a luer lock type of construction, an internal thread construction, a snap-fit type of construction, or any other means to secure the sheath assembly to a viewing instrument. The holding element could also include a gasket attached to the inner surface of, for example, a luer lock which would assist in eliminating leakage between the delivery device and the viewing instrument. It is preferred that the gasket would be made using a soft, pliable material such as a silicone sheet. A collar can also be disposed at the second end of the lumen of the base portion, thereby preventing separation of the shaft portion from the base portion.

Figure 8:
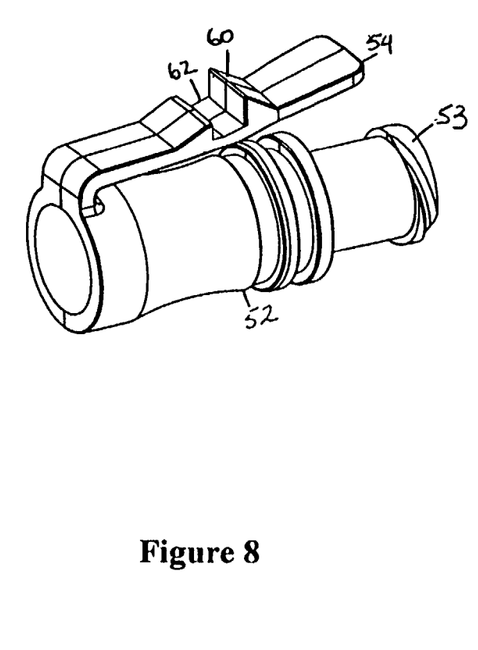
FIG. 8 is a side perspective view of a hub component of a shaft portion of a unitary sheath assembly.

As shown in FIG. 2, the balloon delivery device 14 is configured for insertion 46 through the lumen 28 of the unitary sheath assembly 12. Inflation of a balloon can be by means such as a standard syringe, which can be of a variety of sizes such as a 1 cc-, a 5 cc- or a 10 cc-sized syringe, or any other type of fluid delivery means that can be coupled to the hub 52 of the balloon delivery device 14 as shown in FIG. 8. The hub 52 of the balloon delivery device can also be threaded 53 to fit with standard syringes. Balloons suitable for use in the present invention can be made of an elastic material, such as silicone, that is capable of being easily stretched or expanded while being resistant to breakage or tearing. The balloon structures preferably are self sealing in that after inflation, the balloon is automatically sealed and detachable from the delivery device. Balloon types useful in the present invention are well known in the art and described, for example, in U.S. Pat. Nos. 5,304,123, 5,411,475 and 4,311,146.

A variety of biocompatible fluid materials can be used to fill the balloon depending upon the desired use and preferences of the user. Such materials are well known in the art and include, for example, hydroxyethylmethylacrylate (HEMA), a hydrogel such as polyvinyl pyrrolidone, water, contrast media or saline.

Figure 6:
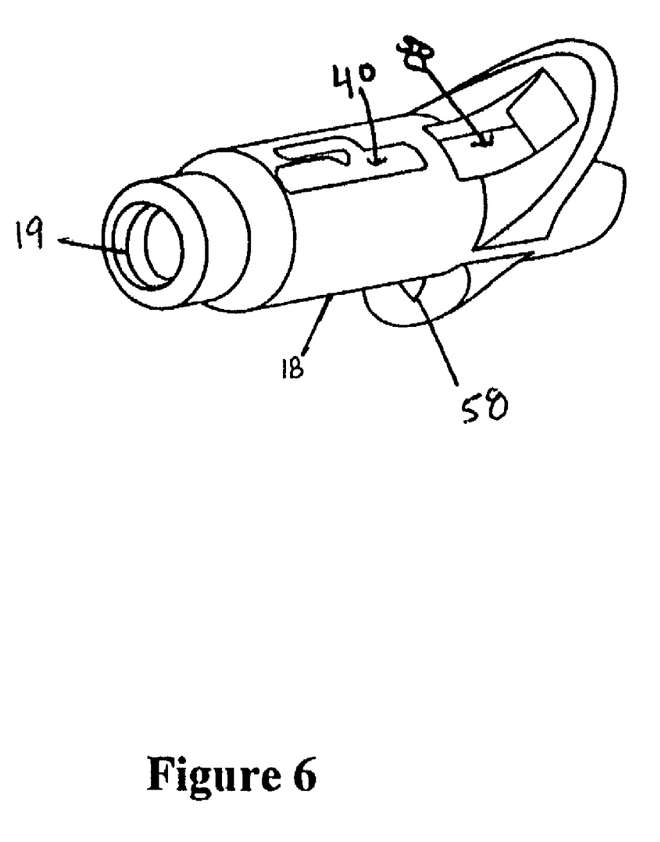
FIG. 6 is a view of a base portion of a unitary sheath assembly including a mating receptacle, holding element and slot opening.
Figure 7:
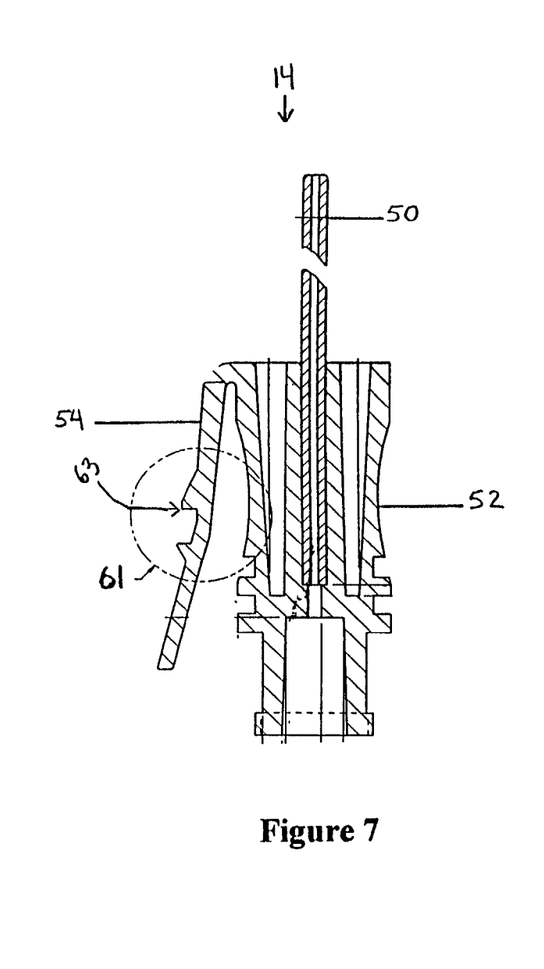
FIG. 7 is a view of a hub component of a shaft portion of a unitary sheath assembly.

FIG. 7 shows a side view of a balloon delivery device. The balloon delivery device 14 includes a catheter 50 component, a hub 52 and a guide tab 54 coupled to the hub 52. The guide tab 54 is flexible and configured 61 so as to allow for easy insertion and removal of the balloon delivery device 14. Depression 63 of the guide tab 54 allows for removal of the balloon delivery device from the unitary sheath assembly. FIG. 8 shows an additional perspective view of a hub 52 of a balloon delivery device 14, including a guide tab 54. The top surface of the guide tab 54 can include raised peaks 60 and notches 62, which when engaged into the base portion 18 of the unitary sheath assembly 12, (FIG. 2) further aid in locking the delivery device in place. This aspect of the present invention further aids in providing a device that is efficient, simple to engage and reliable in delivering a balloon to a target site. Referring to FIG. 6, the base portion 18 of the unitary sheath assembly can have one or more mating receptacle(s) 58 into which the hub 52 of the balloon delivery device 14 slides, (FIG. 2) thereby locking the balloon delivery device 14 in place and preventing possible separation of the catheter from the delivery system during balloon inflation. The location of the mating receptacles can also be designed so as to provide practical versatility to the user. For example, when two mating receptacles are provided, the mating receptacles 58 can be located in direct opposition or at a 180 degree relation to one another. This provides two distinct orientations of the balloon delivery device for insertion into a target site. Additional benefits provided by mating receptacles oriented as such are discussed below in reference to its use with a positioning element.

Figure 9:
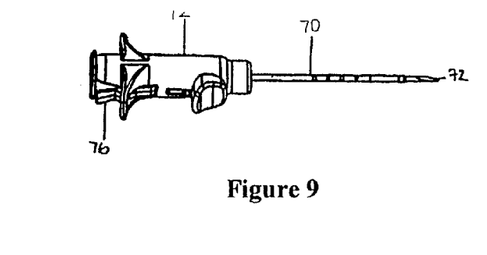
FIG. 9 is a side perspective view of a unitary sheath assembly including a positioning element.
Figure 10:
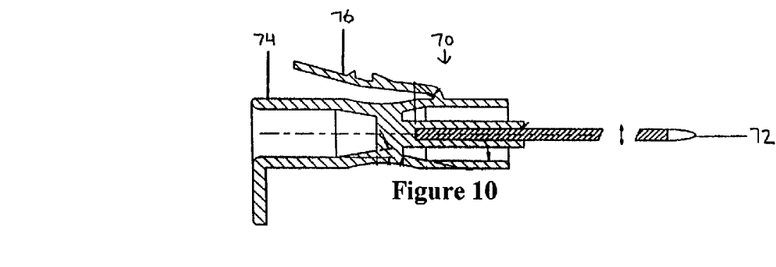
FIG. 10 is a side view of a positioning element of a linear delivery system.
Figure 11:
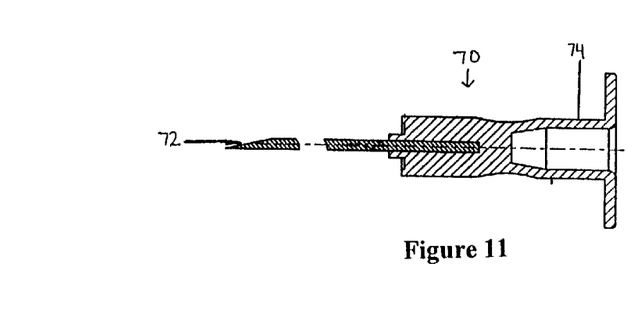
FIG. 11 is an additional side view of a positioning element of a linear delivery system.

FIGS. 10 and 11 show views of a positioning element. As indicated in FIGS. 10 and 11, a positioning element 70 can be included in the linear delivery system. The positioning element 70 has a tip 72 and can be made of a solid wire, configured to allow passage through the lumen 28 of the sheath assembly 12 (FIG. 2). FIG. 9 shows a view of a sheath assembly containing a positioning element 70 having a tip 72. Alternatively, the positioning element 70 can be a hypodermic or cytoscopic needle, so long as the positioning element is sufficiently rigid to allow formation of a pocket at the target site by advancement of the positioning element tip 72 to the target site. In a preferred embodiment, (referring to FIG. 10) the positioning element will also include a hub 74, with a flexible guide tab 76 similar to that described above for the balloon delivery device. The hub 74 with flexible guide tab 76 engages into the mating receptacle 58 (FIG. 6) of the unitary sheath assembly 12, (FIG. 2) which secures the positioning element in place and as with the balloon delivery device, ensures that the positioning element cannot be displaced from the unitary sheath assembly during insertion into the patient. In the case where two mating receptacles are provided, the receptacles can be positioned to provide two distinct orientations of the positioning element 70 when inserted through the unitary sheath assembly. For example, in the case where the tip 72 of the positioning element is beveled (FIG. 11), the positioning needle is commonly inserted by a physician into the target site with the tip 72 of the positioning element 70 oriented bevel-up or at the "twelve o'clock" position. The guide tab 76 is located on the hub 74 of the positioning element in the same orientation as the tip 72 of the positioning element 70 (FIG. 10). Therefore, the orientation of the guide tab 76 (whether it is in a "twelve o'clock, three o'clock, six o'clock, or nine o'clock" orientation), will also indicate the orientation of the bevel or tip 72 of the positioning element 70. This embodiment is equally practical and versatile to both a left-handed or a right-handed user.

Figure 12:
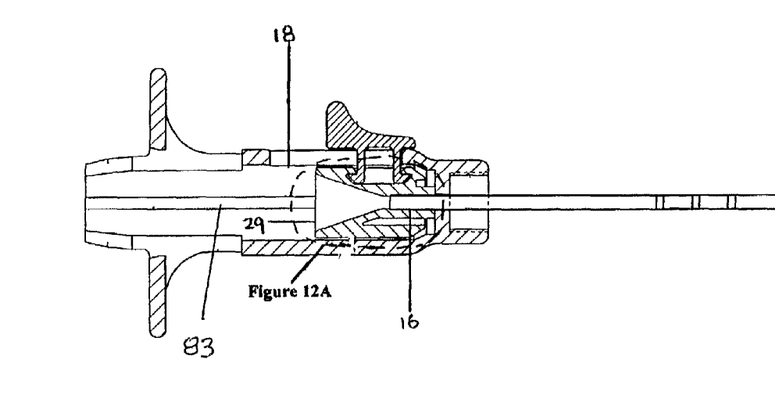
FIG. 12 is a side view of a unitary sheath assembly, with a more detailed view of a connecting element component of a shaft portion (FIG. 12A).
Figure 12A:
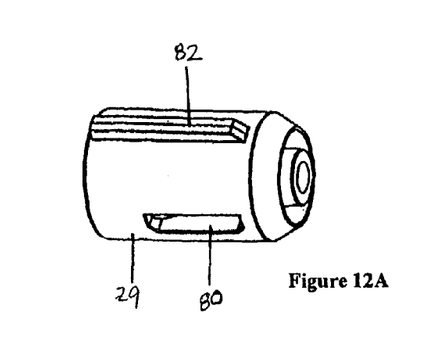

Referring to FIG. 12, in an additional preferred embodiment, the connecting element 29 (FIG. 12A) of the shaft portion 16 of the unitary sheath assembly 12 can also include a ridge 82 that aids in alignment of the shaft 16 within the lumen of the base portion 18. The inner surface of the base portion 18 is also configured to correspond to the ridge 82 so that retraction of the shaft is maintained along a track 83 within the base portion 18 that is a fixed linear or longitudinal axis relative to the unitary sheath assembly.

In a preferred embodiment of a periurethral system for delivery of a 0.9 cc balloon, the shaft portion 16 has a manufacturing specification of 2.750 inches (69.85 mm) in total length, inserting into the shaft hub 26 (FIG. 2) and connecting element 29 by 0.252 inches (6.401 mm), thereby leaving 2.498 inches (63.449 mm) of exposed or visible shaft length. The internal diameter of the shaft portion is 0.072 inches (1.829 mm), or a size sufficient to allow passage of the catheter 50 portion of a balloon delivery device 14 (FIG. 2). The base portion 18 is greater than 1.794 inches (45.568 mm) in length, has a lumen 28 diameter of 0.397 inches (10.084 mm) to 0.428 inches (10.871 mm) and is configured as shown in FIGS. 1 and 2. The slot opening 40 has a length of 0.732 inches (18.593 mm) and is configured as shown in FIG. 4. The retraction tab 34 has a base portion that has a curved upper surface, a base height of 0.348 inches (8.839 mm) and a stem height of 0.247 inches (6.274 mm). The material of the base portion 18, the balloon delivery device hub 52 and flexible guide tab 54, and the positioning element hub 74 and flexible guide tab 76 is a plastic, such as a medical grade polycarbonate. The material of the shaft portion 16, catheter 50, and positioning element 70 is typically made of a flexible material that is sufficiently rigid so as to urge the balloon through the lumen of the catheter 50 and to allow fluid passage. Such a linear delivery system can be provided as a 0.2 cc or a 0.9 cc system that is a disposable, single-use system packaged in individual heat sealed Tyvek® pouches or individual trays. Additionally, the shaft portion 16, catheter 50, and/or positioning element 70 can be made of a less flexible material such as a stainless steel.

The catheter 50 is a two-catheter system where a first, inner catheter 1 is contained within a second, outer catheter 2 (FIG. 2). The outer catheter 2 is of a shorter length than the inner catheter 1, thereby allowing a positive stop for attachment of a balloon to the catheter 50. However, the catheter 50 can also be a single system with an end designed so as to allow relatively easy and stable attachment of the balloon. In some preferred embodiments, the invention contemplates using an inner catheter 1 made of a material such as stainless steel and an outer catheter 2 made from a polymer. In addition, the positing element 70 can be fabricated from a more rigid stainless steel or a more flexible nickel titanium.

In a preferred embodiment of a transurethral system for delivery of a detachable balloon, the longest component will be the positioning element 70. The total length of the positioning element from the beginning of the tip 72 to the end of the hub 74 is approximately 18.50 inches. The length of the exposed portion of the positioning element when engaged and locked into the unitary sheath assembly 18 is approximately 16.30 inches.

The present invention can be used for a variety of medical treatments where implantation of a detachable balloon in a patient is desirable. For example, in the treatment of urinary incontinence, a detachable balloon can be placed in the tissue immediately adjacent to the urethra. The inflated balloon provides pressure external to the urethra, which causes partial closure of the urethra and reduces unwanted fluid leakage from the bladder through the urethra. Alternatively, the present invention can be used in other types of medical treatments where blockage of a duct, vessel, lumen or other tissue is desired, or where the compressive effect of an inflated balloon is desired.

Figure 14:
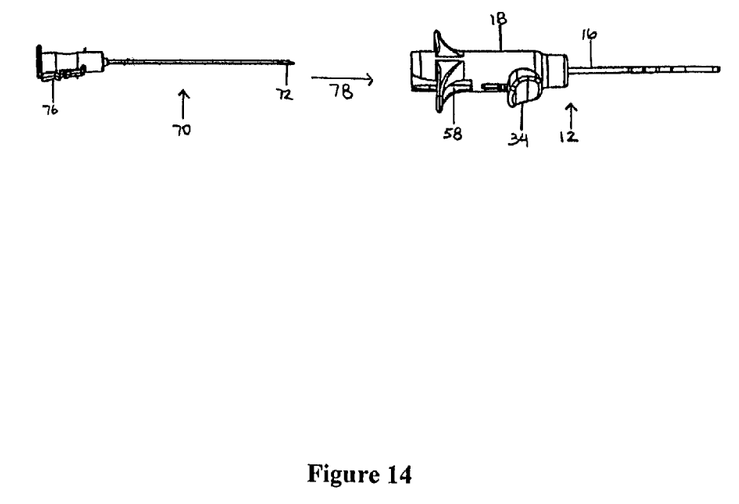
FIG. 14 is an exploded side view of a preferred embodiment of the present invention including a unitary sheath assembly, a balloon delivery device and a positioning element.

Depending upon the target site location and/or physician preference, the linear delivery system can be used in parallel with a viewing instrument or can be passed through a lumen of a viewing instrument. For example, as shown in FIG. 14, in the periurethral method of delivery, the positioning element 70 is first inserted 78 through the shaft 16 of the unitary sheath assembly 12 and "locked" into place into the mating receptacle 58. The unitary sheath assembly 12 and positioning element 70 is then advanced through the patient's tissue parallel to the urethra to the target site. The desired target site and correct positioning of the assembly is observed using a viewing instrument passed through, for example, the urethra. In transurethral delivery, the positioning element 70 is passed through the shaft 16 of the unitary sheath assembly 12 until the positioning element tip 72 extends beyond the distal end of the sheath assembly 12, and is locked into place in a mating receptacle 58 by the flexible guide tab 76. The unitary sheath assembly 12 and positioning element 70 is passed through the lumen of a viewing instrument such as a cytoscope, The viewing instrument, sheath assembly and positioning element, together are advanced to the target site in vivo.

Various materials can be used for constructing the shaft portion 16 and positioning element 70, depending upon the particular method of delivery. For example, if the linear delivery system is to be passed through a viewing instrument, a flexible material such as a nickel titanium alloy is desirable. Alternatively, if the linear delivery system is to be passed directly through a patient's tissues, a less flexible material such as stainless steel is preferable.

Method for Deployment of a Linear Delivery System

Figure 13:
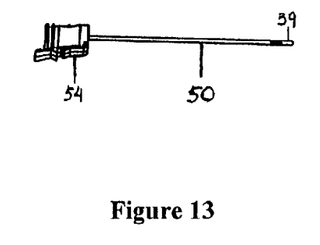
FIG. 13 is a view of a balloon delivery device having a balloon.

The present invention also contemplates a method of using a linear delivery system for deployment of a detachable, inflatable balloon at a target site in a patient. The method includes providing a linear delivery system 10 as shown in FIGS. 13 and 14. The positioning element 70 is passed through the inner lumen of the sheath assembly 12 until the positioning element tip 72 extends beyond the distal end of the sheath assembly 12, and is locked into place by the flexible guide tab 76. The positioning element tip is advanced to the target site in vivo. By depressing the guide tab 76 and pulling back on the hub 74 (not shown) of the positioning element 70, the positioning element is then withdrawn from the sheath assembly with the sheath assembly remaining fixed at the target site. There is little or no risk of the positioning element separating prematurely from the sheath assembly because it is held securely in place by the flexible guide tab 76 and mating receptacle 58.

Once the positioning element is removed from the sheath assembly, a balloon delivery device 14 with a balloon 39 coupled to the catheter 50 component of the delivery device (FIG. 13) is passed through the sheath assembly. The balloon delivery device is advanced through the sheath assembly until the flexible guide tab 54 (FIG. 13) engages into the mating receptacle 58 (FIG. 14) of the unitary sheath assembly base 18. This aspect of the invention prevents the catheter of the balloon delivery device from separating from or being displaced from the sheath assembly during balloon inflation. The retraction tab 34 on the base portion 18 of the unitary sheath assembly 12 is then retracted backward toward the first end 30 of the base portion 18 to expose the balloon to the target site in vivo (as shown in FIG, 1). The balloon is inflated and detached and the delivery system is removed.

The methods and systems of the present invention provide simple, accurate and stable balloon deployment at the target site in vivo. The features of the invention, as described herein, provide a linear delivery system that is less awkward or cumbersome for the physician to use.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A linear delivery system comprising:
   (i) a unitary sheath assembly having
      a base portion including a housing having first and second ends, a lumen extending through said housing, a slot located on the housing for receiving a stem, said slot further including a bendable tong portion, and a stem receiving element at said second end;

a retractable shaft portion including an inner lumen extending between a proximal end and a distal end and in fluid communication with the lumen of the base portion, and a shaft hub coupled to the proximal end fo the retractable shaft portion and the second end of the base portion; and a retraction tab disposed on said base portion, said retraction tab slidably moveable along a longitudinal axis thereof, said retraction tab including lower stem means received by said stem receiving element through said slot for securely attaching said retraction tab to said base portion wherein upon axial movement of the retraction tab alone the longitudinal axis, the shaft is withdrawn from the second end of the base toward the first end of the base, and further wherein engagement of the retractable tab in the bendable tong inhibits movement of the delivery device relative to the sheath assembly; and (ii) a balloon delivery device configured for insertion through the sheath assembly, the device having a catheter, a hub and a guide tab coupled to the hub.

2. The system of claim 1 further comprising visual indicators disposed on the sheath assembly for providing an indication of a penetration depth of the unitary sheath assembly into a patient.

3. The system of claim 1, wherein the unitary sheath assembly further comprises an holding element for attachment of the assembly to a viewing instrument.

4. The system of claim 3, wherein the holding element further comprises a luer lock.

5. The system of claim 1, wherein the base portion of the unitary sheath assembly is configured such that movement of the delivery device through the sheath assembly is maintained in a longitudinal axis by movement of the guide tab within the receptacle.

6. The system of claim 1 wherein a lumen collar of the base portion prevents separation of the shaft portion from the base portion.

7. The system of claim 1 further comprising a positioning element for establishing a pocket at a target site in vivo.

8. The system of claim 7 wherein the positioning element is a needle.

9. A method of deploying a detachable, inflatable balloon at a target site in a patient in vivo, comprising:

providing a unitary sheath assembly having a base portion including a housing having first and second ends, a lumen extending through said housing, a slot located on the housing for receiving a stem, said slot further including a bendable tong portion, and a stem receiving element at said second end;

a retractable shaft portion including an inner lumen extending between a proximal end and a distal end and in fluid communication with the lumen of the base portion, and a shaft hub coupled to the proximal end fo the retractable shaft portion and the second end of the base portion; and a retraction tab disposed on said base portion, said retraction tab slidably moveable along a longitudinal axis thereof, said retraction tab including lower stem means received by said stem receiving element through said slot for securely attaching said retraction tab to said base portion, wherein upon axial movement of the retraction tab along the longitudinal axis, the shaft is withdrawn from the second end of the base toward the first end of the base, and further wherein engagement of the retractable tab in the bendable tong inhibits movement of the delivery device relative to the sheath assembly;

passing a positioning element tip through the inner lumen of the sheath assembly until the positioning element tip extends beyond the distal end of the sheath assembly;

advancing the positioning element tip to the target site in vivo;

withdrawing the positioning element tip from the sheath assembly such that the sheath assembly remains fixed relative to the target site;

passing a balloon coupled to a delivery device through the unitary sheath assembly;

retracting the shaft of the sheath assembly by actuating said retraction tab axially along the longitudinal axis of said base portion such that the balloon is exposed to the target site in vivo; and inflating and detaching the balloon.

10. The method of claim 9, wherein passage of a positioning element through the sheath further comprises passing a guide tab disposed on a hub of the positioning element along at least one mating receptacle disposed on a base portion of the sheath assembly such that passage of the positioning element through the sheath is directed by a linear motion.

11. The method of claim 9, wherein passage of the delivery device through the unitary sheath assembly further comprises passing a guide tab disposed on a hub of the delivery device along a receptacle disposed on a base portion of the sheath assembly such that passage of the delivery device through the sheath is directed by a linear motion.

* * * * *